United States Patent [19]
Kim et al.

[11] Patent Number: 5,585,547
[45] Date of Patent: Dec. 17, 1996

[54] OXYGEN SENSOR PROBE FOR BOILER

[75] Inventors: Ki S. Kim; Han S. Song, both of Taejon; Geun C. Yum, Seoul; Dae J. Ko, Taejon, all of Rep. of Korea

[73] Assignee: Ssangyong Cement Industrial Co., Ltd., Seoul, Rep. of Korea

[21] Appl. No.: 369,537

[22] Filed: Jan. 5, 1995

[30] Foreign Application Priority Data

Jan. 6, 1994 [KR] Rep. of Korea ............................ 94-130
Jan. 12, 1994 [KR] Rep. of Korea ............................ 94-357

[51] Int. Cl.$^6$ ............................... G01N 27/26; H01L 7/00
[52] U.S. Cl. ..................... 73/31.05; 73/23.2; 73/23.32; 204/426; 204/428
[58] Field of Search ................................. 73/31.05, 23.2, 73/23.31, 23.32; 204/424, 428, 429, 427, 426

[56] References Cited

U.S. PATENT DOCUMENTS

| | | | |
|---|---|---|---|
| 4,415,878 | 11/1983 | Novak ........................................ | 338/34 |
| 4,786,398 | 11/1988 | Wertheimer et al. .................... | 204/427 |
| 4,883,643 | 11/1989 | Nishio et al. ............................. | 422/94 |
| 4,944,861 | 7/1990 | Reber ......................................... | 204/428 |
| 4,956,072 | 9/1990 | Kojima et al. ............................ | 204/424 |
| 5,073,247 | 12/1991 | Weyl .......................................... | 204/428 |
| 5,203,983 | 4/1993 | Ohyama et al. .......................... | 204/427 |
| 5,296,112 | 3/1994 | Seger et al. ............................ | 204/153.18 |
| 5,310,575 | 5/1994 | Friese et al. ............................ | 427/126.3 |

Primary Examiner—Hezron E. Williams
Assistant Examiner—J. David Wiggins
Attorney, Agent, or Firm—Finnegan, Henderson, Farabow, Garrett & Dunner

[57] ABSTRACT

An oxygen sensor probe for a boiler including a U-shaped zirconia element that is to be brought in contact with an exhaust gas in the interior of a cylindrical probe body attached to a plug and arranged together with a thermocouple in the longitudinal direction of the body. A heater for heating the element is provided around the periphery of the element and a protective filter is provided on the top portion of the body. The probe is characterized by the U-shaped zirconia element 11 being located at an upper end of the probe body 12 with its concave open portion 11' facing upwards to be contacted with the exhaust gas while its convex closed portion 11" faces downward to be confronted with the thermocouple 16. Also included is packing material 15 for sealing the space between the upper end 13 of the element 11 and the plug 14, a heater 17 located in the periphery of the closed portion 11" of the element 11 for heating the element, and a support 19 located between the plug 14 and the heater 17 for protecting an electrode contact and supporting the heater.

9 Claims, 3 Drawing Sheets

OXYGEN SENSOR PROBE FOR BOILER

BACKGROUND OF THE INVENTION

1. Field of the Invention

The present invention relates to an oxygen sensor probe for a boiler, and in particular to an oxygen sensor probe suitable for measuring oxygen in the exhaust gas being discharged from a heating engine such a small boiler.

2. Description of the Prior Art

Recently, it has become considerably important to control harmful gases and floating particles included in exhaust gas being discharged from various heating engines as well as boilers and automobile engines in view of the fact that atmospheric air pollution has become a very serious problem.

An oxygen sensor, especially, is used for measuring the amount of oxygen in the exhaust gas in order to control and maintain a ratio of air to fuel and to control and maintain the operation of heating engines such as a boiler at an optimum state thereof, and for controlling the amount of oxygen supplied at an appropriate level.

At present, most oxygen sensors for a boiler use stabilized zirconia as an element of the oxygen sensor.

As shown in FIG. 3, a conventional zirconia oxygen sensor has a U-shaped element of zirconia inserted into a probe shell made of strong anti-corrosive stainless steel. It comprises a zirconia oxygen sensor element 31 of U-shape, a heater 32, a plug 33, and a probe shell 34.

The convex closed portion 31' of the zirconia element 31 is arranged so as to contact with the exhaust gas to be measured, and a thermocouple 36 is inserted into the concave open portion 31" from its opposite end, thereby giving an exposure to the air as a reference gas.

The lower end 37 of the U-shaped zirconia element 31 is attached to the inside wall of the plug 33 which is also made of a strong anti-corrosive stainless steel. The heater 32 is installed in the inside wall of the probe shell 34, and the upper portion of the probe shell 34 in contact with the exhaust gas is covered with a protective filter 35.

Accordingly, the space between the zirconia element and the probe shell is completely cut off from the outside by the protective filter and plug so that the exhaust gas and air are completely isolated from one another in the sensor.

FIG. 4 shows the structure of another conventional oxygen sensor. The oxygen sensor has separate heater tubes 32' on the inside of the probe shell 34, instead of the heater being located on the inside wall of the probe shell.

As shown in FIGS. 3 and 4, the conventional oxygen sensor is an insertion-type sensor, in which the element is inserted into the probe shell made of stainless steel. Hence, it has the disadvantage of not being useful for boilers of 5 tons or less because of its large scale.

Moreover, the zirconia element of the conventional oxygen sensor needs to be long in order to provide room for the heater as shown in FIG. 3, and the outer diameter of the probe shell needs to be large to accommodate the heater tubes as shown in FIG. 4.

While measuring the amount of oxygen in the exhaust gas by using the oxygen sensor, the exhaust gas should not be in contact with air. Therefore, it is very important to provide an adequate seal between the lower end of the zirconia element and the plug to completely isolate the exhaust gas from the air in the sensor.

Since the exhaust gas contains a lot of various corrosive gases, the material of the plug and the probe shell have generally been of a strong anti-corrosive stainless steel.

However, the thermal expansion coefficient of stainless steel is very large, as much as $19 \times 10^{-6}$ so that it is difficult to bind the stainless steel with the zirconia element, which has a thermal expansion coefficient of about $9 \times 10^{-6}$.

The reason is explained in detail as follows. The zirconia element and the plug made of stainless steel are bound in a circumferential direction. In this case, there occurs an inevitable difference of thermal expansion coefficient between them of up to $10 \times 10^{-6}$. If the temperature of the zirconia element and stainless steel is 800° C. or more, a difference of distortion to an extent of $8 \times 10^{-3}$ (derived from a difference of thermal expansion coefficient) may occur. No materials can resist such distortion. Further, since the zirconia element is cylindrical in shape, more stress is concentrated in the circumferential direction than the vertical direction, and a shear stress occurs between the attached portion of the element and its portion exposed to the air. As a result, a fracture may occur.

In order to solve this problem, an attempt has been made to alter the zirconia element from a cylinder to a disk. A portion to be exposed to the air is removed, and the outside metal cylinder is thin enough to be easily distorted. However, the method is not desirable because the binding portion is effected by heating the binding portion at a temperature of 700° C. or more, and there is a problem in connecting the electrode because of high temperature.

Stainless steel can be used even under an inferior condition due to its beneficial properties of being strongly resistant to chemical agents and corrosion. Accordingly, an attachment of ceramic to stainless steel has been attempted since its range of application will be enlarged if the attachment with ceramic is possible. Ceramic may be used where only the strength of the attachment is important, but not where a high level of air tightness is required. However, the technology for an air tight attachment between a U-shaped zirconia element and stainless steel has not yet been developed.

In particular, in case of a zirconia oxygen sensor for a boiler, in which the zirconia element is heated by using a heater, the overall size and shape of the sensor probe will depend on the sealing method used.

The following sealing methods have been reported:

1) extending the length of the U-shaped zirconia element and measuring the amount of oxygen at a discharging portion of the exhaust gas, so that the binding portion is exposed to the atmosphere to prevent thermal shock.

2) using a talc powder between the U-shaped zirconia element and the plug instead of attaching the zirconia element directly to the plug; and 3) sealing a disk-type zirconia element to the plug in the form of a tube by using materials such as glass or a brazing alloy.

However, in the method of 1), the size of the sensor becomes too large due to the extended length of the zirconia element, and it is difficult to select a sealing material suitable for the temperature of the sealing portion. Furthermore, the sealing function of the sealing material can be a problem if there is a difference in pressure between the inside of the boiler and the atmosphere of over 500 mm $H_2O$.

The method of 2) has the feature that the sealing portion can resist a high temperature of 500° C. or more and the size of the sensor is miniaturized to a certain extent. On the other hand, the size and thickness of the outer plug needs to be enlarged to obtain an air-tight seal that can enclose the strong pressure deriving from the filling of the talc powder with strong pressure. It results in an increase in the size and weight of the sensor. If a difference in the pressure between the atmosphere and the inside of the boiler is over 500 mm $H_2O$, the sensor is hard to use because the airtight sealing is not equal to the attached version.

The method of 3) in which a disk-type zirconia element is attached to a tube-type plug has no problem of sealing. However, this method has the disadvantage that the life of the sealing portion is shortened when heated to a high temperature of over 700° C. since both the zirconia element and the sealing portion are heated by a heater, and the sensor deteriorates when heated below this temperature. Since the electrode is connected by mechanical pressing at the above temperature, the connection of the electrode becomes unstable. Moreover, the miniaturization of the disk element is limited because the strength and size of the disk are given much weight. Consequently, the operation becomes inconvenient because of the increased weight of the probe, an error in electromotive force occurs due to the unstable electrode, and the life of the product is shortened.

In particular, in the case of using a glass or brazing alloy, a compressive stress is located on the portion of the zirconia element, thereby giving a shear stress between its sealed outer and inner surfaces to be exposed to the atmosphere. Consequently, a cracking and/or rupture may occur in the sealed portion.

On the other hand, the durability of the oxygen sensor probe is very important. If the durability of the oxygen sensor probe increases two times, it is equivalent to two oxygen sensor probes. The most problems with durability are a high corrosion (resulting from reacting platinum with $SO_2$ in the exhaust gas in the vicinity of temperature of 300° C. to 400° C.) and a low corrosion (resulting from reacting platinum with $H_2SO_4$ in the exhaust gas in the vicinity of temperatures of 150° C. to 300° C.). Since $SO_2$ or $H_2SO_4$ in the exhaust gas will react with the platinum, the platinum electrode will deteriorate. To prevent this corrosion, a plasma jet coating with spinel can be used.

However, the contact of platinum and exhaust gas cannot be completely prevented since spinel is porous. Further, the reaction rate in the sensing portion will drop on account of the above coating.

SUMMARY OF THE INVENTION

The present inventors have worked extensively to overcome these problems of the prior art. In accordance with the invention, the position of the element of the U-shaped zirconia oxygen sensor in the interior of the probe shell has been oppositely changed in comparison with a conventional zirconia oxygen sensor. Sealing is carried out by using an intermediate acting as a buffer between the zirconia element and the plug. In this invention, to prevent corrosion, the exposed portion of the element at low temperature is coated with glass. By doing so, the sensor may be miniaturized, and it is simple to operate. Furthermore, the characteristics of the sensor may be improved, and the operation energy of the heater may be reduced. In addition, the durability of the oxygen sensor may be relatively extended.

The object of the present invention is to provide an oxygen sensor probe suitable for use with a small boiler by altering the position of the U-shaped zirconia element toward the upper portion of the probe body.

Another object of the present invention is to provide an oxygen sensor probe, in which the plug of stainless steel and zirconia element are sealed using an intermediate made of a metal or an alloy similar to the thermal expansion coefficient of the zirconia element.

A further object of the present invention is to provide an oxygen sensor probe, in which the coating is formed with a certain thickness when the intermediate is sealed to prevent corrosion by the exhaust gas.

Yet another object of the present invention is to provide an oxygen sensor probe, in which the low temperature exposed portion of the element is coated to prevent a deterioration of the platinum electrode due to the corrosion with $SO_3$.

Yet another object of the present invention is to provide an oxygen sensor probe, in which the characteristics of electromotive force is good, the anti-corrosive property and the durability are improved and the energy is greatly reduced.

This invention provides an oxygen sensor probe including a U-shaped zirconia element that is to be brought into contact with an exhaust gas in the interior of a cylindrical probe body attached to a plug and arranged together with a thermocouple in the longitudinal direction of the body, a heater for heating the element around the periphery of the element, and a protective filter covering the top portion of the body, characterized in that the probe comprises a U-shaped zirconia element located at an upper end of the body, its concave open portion of the element facing upwards to be in contact with the exhaust gas while its convex closed portion faces downward to be confronted with the thermocouple; means for sealing the space existing between the upper end of the element and the plug having a hole in its mid portion to prevent the occurrence of thermal stress; heating means located in the periphery of the closed portion of the element for heating the element; and support means located between the plug and the heating means for protecting an electrode contact and supporting the heating means.

According to the present invention, the sealing means consists of nickel, titanium or an alloy thereof, and has a thermal expansion coefficient of $7\times10^{-6}$/° C. to $13\times10^{-6}$/° C. similar to that of the element. The space between the sealing means and the top end of the element are joined with glass or a brazing alloy.

Furthermore, the outer wall surface of the sealing means and the inner wall surface of the plug, and the outer surface of the plug and the inner surface of the top end of the body are respectively formed with screw threads so that they can be sealed with each other. The upper surface of the sealing means and the lower surface of a flange of the metal plug are joined by means of an O-ring made of copper, aluminum or mica.

According to the present invention, the sealing means is heat-treated in the range of temperature of 600° C. to 1200° C. to prevent corrosion, thereby forming an oxidated coating of 50 to 200 μ thereon. The element is coated with a glaze material to prevent corrosion of the portions except for a portion being heated by the heating means.

The above objects, characteristics and advantages of the present invention may be easily understood by referring to the following descriptions and the attached drawings.

BRIEF DESCRIPTION OF THE DRAWINGS

How the foregoing objects and advantages are attained will appear more fully from the following description referring to the accompanying drawings, in which.

DESCRIPTION OF THE PREFERRED EMBODIMENT(S)

Figure 1:
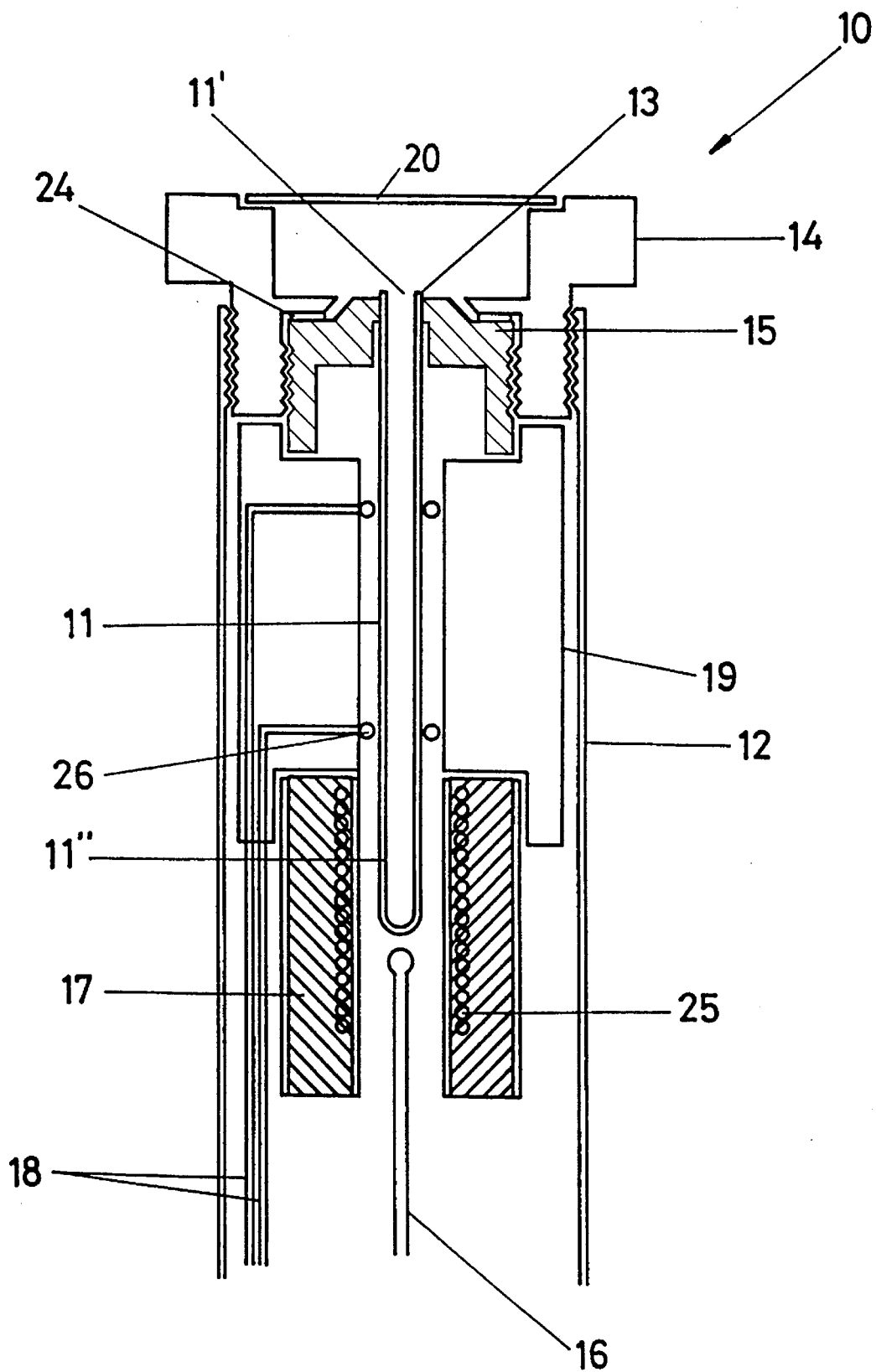
FIG. 1 is a vertical, longitudinal sectional view illustrating an oxygen sensor probe for a boiler according to the invention.
Figure 2:
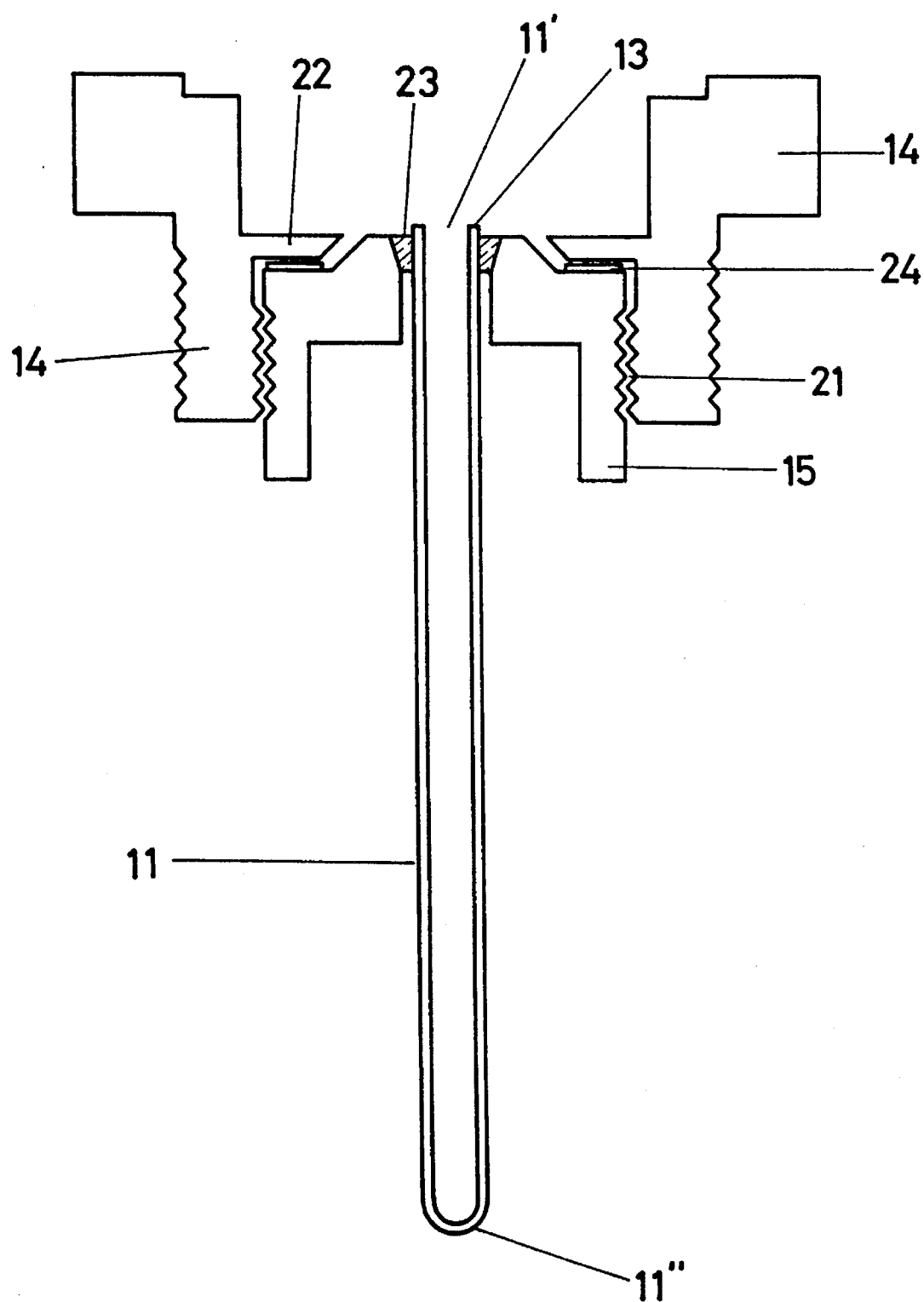
FIG. 2 is an enlarged vertical, longitudinal sectional view illustrating the jointing portion of the element of the oxygen sensor probe shown in FIG. 1.
Figure 3:
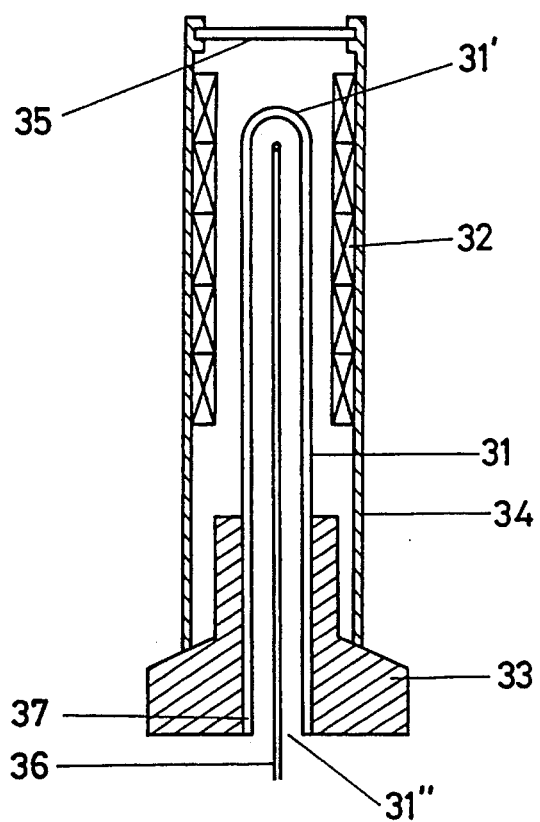
FIG. 3 is a vertical section view illustrating a conventional oxygen sensor probe for a boiler.
Figure 4:
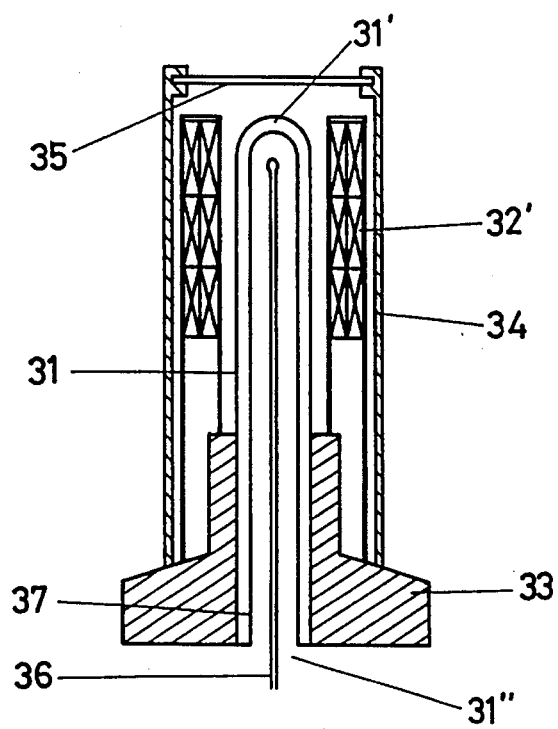
FIG. 4 is a vertical section view illustrating another conventional oxygen sensor probe for a boiler.

With reference to the attached drawings, the present invention is concerned with an oxygen sensor for a small boiler, wherein a small U-shaped zirconia element is inserted, with sealing, into a probe body fabricated of a stainless steel. FIG. 1 is a vertical, longitudinal sectional view illustrating the oxygen sensor probe for a boiler according to the invention. FIG. 2 is an enlarged vertical, longitudinal sectional view illustrating a jointing portion of an element of the oxygen sensor probe shown in FIG. 1.

In FIG. 1, a U-shaped zirconia element 11 of an oxygen sensor probe 10, according to the present invention, is located at the top end of a cylindrical probe body 12 to be contacted with the exhaust gas along its longitudinal axis. The concave open portion 11' of the element faces upward while its convex closed portion 11" faces downward.

The top end 13 of the concave open portion 11' of zirconia element 11 is joined to an annular plug 14 by sealing means or packing material 15 as an intermediate, the top end of the probe body 12 being sealed to the plug 14.

On the other hand, the closed portion 11" of the zirconia element 11 is confronted with a thermocouple 16 and is located at the mid portion of heaters 17 which also have a cylindrical shape. Heaters 17 are supported by a heater support 19, in which a lead wire 18 to measure electromotive force is inserted. Number 25 is a heater line and number 26 is a spring-like shape of lead wires which contacts an electrode.

A specific improvement of the invention is that the U-shaped zirconia element is located at the top of the probe body 12 to be contacted with the exhaust gas, and an open portion of the element faces upward while its closed portion faces downward. Additionally, the top end 13 of the zirconia element 11 is substantially sealed tightly to the plug 14 by means of the packing material 15 and a protective filter 20 covers the top end of the probe body.

As a packing material, a metallic material such as nickel, titanium or an alloy thereof having a thermal expansion coefficient similar to that of zirconia, for example $7 \times 10^{-6}/°$ C. to $13 \times 10^{-6}/°$ C. preferably may be used. This packing material effectively prevents the occurrence of thermal stress between the zirconia element and the probe made of stainless steel.

The packing material 15 of the invention is joined to the top end 13 of the zirconia element by using a glass or brazing alloy 23 having a thermal expansion coefficient similar to that of a U-shaped zirconia element 11 as shown in FIG. 2. Further, the outer side of the packing material 15 screws into the inner side of the plug 14 made of stainless steel by appropriate screw threads 21 being formed on each surface thereof. The upper side of the packing material 15 also joins with the lower side of a flange 22 of the plug 14 through the medium of an O-ring 24 made of a material, such as copper, aluminum or mica, so that the packing material 15 seals tightly with the plug 14. As a result, a complete sealing may be accomplished. The present invention has the advantage of being capable of preventing the formation of stress by sealing the zirconia element 11 and the plug 14 by using the packing material 15 formed with screw threads thereon and the O-ring 24 having a good elasticity.

In accordance with the present invention, to avoid deterioration of the platinum electrode under high temperature corrosion and lower temperature corrosion that can result from the reaction of $SO_2$ and $H_2SO$ in the exhaust gas with the platinum of the above electrode, the portion of the element which is exposed to the exhaust gas at the condition of low temperature except for the high temperature portion which is heated by the heater 17, is coated with a glaze material such as glass powder. Thus by covering the zirconia element with glass, except the sensing portion, corrosion can be prevented.

On the other hand, when packing material 15 according to the present invention is exposed to $SO_2$ in the exhaust gas for a long time, corrosion may occur. Such corrosion also affects the life of the oxygen sensor. For the above reason, the packing material 15 used in the invention may be heat-treated under an oxidation atmosphere of a high temperature of 600° C. to 1200° C. to provide an oxidized coating thereon having a thickness of 50 to 200 μm.

In accordance with the invention, sealing with the glass or brazing alloy, the glaze coating on the low temperature portion of the element and the formation of the oxidized coating on the packing material may be simultaneously conducted by heat-treating.

In the oxygen sensor probe, according to the present invention, the concave open portion of the element is attached to the top end of the probe body so as to face toward the exhaust gas. Therefore, the size of the sensor may be substantially reduced to an outer diameter of 3 to 100 mm and a length of 20 to 100 mm. Thus, the cost may also be reduced since the sensor itself is smaller.

Furthermore, according to the present invention, since the sensor is fixed to the end of shell so that the concave open portion of the element faces toward the exhaust gas after greatly reducing the size of the sensor, it is possible to attach a small heater thereto. Thus, it is possible to fabricate a slim body for the probe.

In particular, the electrode contact 26 is positioned between the exhaust gas and the heater after installing a small heater contrary to conventional probes and is protected by the heater support which supports the heater, so that it is possible to take out two contacts.

The oxygen sensor probe according to the present invention, is substantially smaller than conventional probes. However, the electromotive force property is very good, and the quality, durability and anti-corrosion properties are also improved. Furthermore, the sensor probe may be installed, and the cost may be reduced.

With reference to an exemplary embodiment set forth in the following, the apparatus of the invention will now be further clarified and explained.

EXAMPLE

A zirconia element, having an outer diameter of 6.0 mm and a length of 45 mm, and a packing material made of Ti alloy, having a thermal expansion coefficient similar to the zirconia element, an outer diameter of 9.0 mm and an inner diameter the same as the outer diameter of the above zirconia element, and having screw threads formed on an outer side thereof were sealed together using a sealing material. As the sealing material, a glass was used consisting of 60% by weight of $SiO_2$, 10% by weight of $Al_2O_3$, 10% by weight of $K_2O$, 10% by weight of $NaO$, 9% by weight of $B_2O_3$ and 1% by weight of $CaO$ and having a thermal expansion coefficient similar to Ti/alloy and a melting point of 800° C.

As a coating material for the exposed lower temperature portion of the zirconia element, a glass consisting of 50% by weight of $SiO_2$, 15% by weight of $Al_2O_3$, 20% weight of $ZrO_2$, 10% by weight of $K_2O$ and 5% by weight of $SnO_2$, and having a thermal expansion coefficient similar to the zirconia element, a melting point of 1000° C. and a good wetting property with platinum, was used and heat-treated under an oxidative atmosphere of 850° C.

As a result, a dense oxidized coating of 60 μ was formed on the surface of Ti alloy and the coating for the zirconia element was good.

The prepared element was attached to a probe body made of stainless steel, and a heater was provided therewith to form an oxygen sensor probe.

The physical properties of the thus fabricated oxygen sensor probe were compared with those of three conventional ones.

In the following Table 1, Example is the probe of the invention, prior art 1 is a probe prepared by sealing method 1), prior art 2 is a probe prepared by sealing method 2), and prior art 3 is a probe prepared by sealing method 3).

As shown in Table 1, the probe of the invention, which can survive harsh environments such as high pressure in boilers, is very precise and consumes low amounts of energy.

TABLE 1

| Physical Properties | Example | Prior Art 1 | Prior art 2 | Prior art 3 |
| --- | --- | --- | --- | --- |
| Available exhaust gas pressure | ±3000 mmH$_2$O | ±500 mmH$_2$O | ±500 mmH$_2$O | ±3000 mmH$_2$O |
| Length of probe | about 30 mm | about 60 mm | about 50 mm | about 58 mm |
| Weight of probe | 1.7 kg | about 4 kg | about 4 kg | about 5 kg |
| Permissible errors of electromotive force | ±0.1% | ±0.2% | ±0.2% | ±0.2% |
| Durability | very good | little poor | good | good |
| Power consumption of heater | very few | few | much | much |

Although the invention has been described with references to specific embodiments, it is understood that such embodiments may be altered, modified or changed by those skilled in the art without departing from the spirit and the scope of the invention as hereinafter claimed.

What is claimed is:

1. An oxygen sensor probe for a boiler comprising:

a cylindrical probe body having an upper end and a lower end;

a U-shaped zirconia element located in the interior of the body and extending linearly along the axis of the body, said element having an open end facing toward the upper end of the body and a convex closed end facing toward the lower end of the body, said open end of the element being adapted to be brought into contact with an exhaust gas;

a thermocouple adjacent to and axially-aligned with the convex closed portion of the element for measuring the temperature of ambient air as a reference gas;

an annular plug sealingly joined to the upper end of the probe body;

sealing means located between the outside of the open end of the element and the inside of the annular plug, said sealing means comprising a packing material made of nickel, titanium, or an alloy thereof and having a thermal expansion coefficient of from $7\times10^{-6}/°$ C. to $13\times10^{-6}/°$ C.; and heating means located in the body and around the periphery of the element adjacent its closed end for heating the element.

2. The oxygen sensor probe of claim 1, including a protective filter covering the upper end of the probe body.

3. The oxygen sensor probe of claim 1, including means located between said plug and said heating means in an axial direction for providing an electrode contact and for supporting said heating means.

4. The oxygen sensor probe of claim 1, wherein the sealing material and the outside of the open end of said element are joined with a glass or brazing alloy.

5. The oxygen sensor probe of claim 1, wherein an outer wall surface of said packing material and an inner wall surface of said plug are threadably connected to each other.

6. The oxygen sensor probe of claim 1, including an O-ring seal of copper, aluminum, or mica between an upper surface of said packing material and a lower surface of a flange of said plug.

7. The oxygen sensor probe of claim 1, wherein said packing material has an oxidized coating thereon of from 50 to 200 µ by heat-treating it in the range of from 600° to 1200° C. to prevent corrosion thereof.

8. The oxygen sensor probe of claim 1, wherein said element is coated with a glaze material except for the portion being heated by said heating means to prevent corrosion thereof.

9. The oxygen sensor probe of claim 1, wherein an outer surface of said plug and an inner surface of the upper end of said body are threadably connected to each other.

* * * * *